US012667718B2

(12) United States Patent
Maggi

(10) Patent No.: US 12,667,718 B2
(45) Date of Patent: Jun. 30, 2026

(54) SYSTEM AND METHOD FOR IMPLANTABLE NEURAL SENSING AND STIMULATING PROBES

(71) Applicant: Ecate LLC, Los Angeles, CA (US)

(72) Inventor: Alessandro Maggi, Los Angeles, CA (US)

(73) Assignee: ECATE LLC, Los Angeles, CA (US)

( * ) Notice: Subject to any disclaimer, the term of this patent is extended or adjusted under 35 U.S.C. 154(b) by 412 days.

(21) Appl. No.: 18/137,614

(22) Filed: Apr. 21, 2023

(65) Prior Publication Data

US 2024/0189582 A1    Jun. 13, 2024

Related U.S. Application Data

(60) Provisional application No. 63/432,294, filed on Dec. 13, 2022.

(51) Int. Cl.
  *A61N 1/05*     (2006.01)
  *A61N 1/36*     (2006.01)
(52) U.S. Cl.
  CPC ....... *A61N 1/0551* (2013.01); *A61N 1/36007* (2013.01); *A61N 1/36135* (2013.01)
(58) Field of Classification Search
  CPC .............. A61N 1/0551; A61N 1/36007; A61N 1/36135; A61N 1/36139
  See application file for complete search history.

(56) References Cited

U.S. PATENT DOCUMENTS

| 2004/0006262 A1* | 1/2004 | Guy ....................... A61B 5/411 600/345 |
| 2014/0222123 A1* | 8/2014 | Cui .................... G01N 33/4836 29/842 |
| 2017/0231518 A1* | 8/2017 | Dayeh ................. B81C 1/00111 600/544 |
| 2020/0298005 A1* | 9/2020 | Howard ............... A61B 5/4836 |

FOREIGN PATENT DOCUMENTS

WO    WO-2020092652 A1 *   5/2020   ........... A61N 1/0556

OTHER PUBLICATIONS

Abbott, Jeffrey et al., "A nanoelectrode array for obtaining intracellular recordings from thousands of connected neurons," Nature Biomedical Engineering, vol. 4, Feb. 2010, pp. 232-241.
Hai, Aviad et al., "Long-Term, Multisite, Parallel, In-Cell Recording and Stimulation by an Array of Extracellular Microelectrodes," J. Neurophysiol 104:559-568, 2010.
Liu, Ren et al., "High Density Individually Addressable Nanowire Arrays Record Intracellular Activity from Primary Rodent and Human Stem Cell Derived Neurons," Nano Lett. Apr. 6, 2017.
Robinson, Jacob T. et al., "Vertical nanowire electrode arrays as a scalable platform for intracellular interfacing to neuronal circuits," Nature Nanotechnology vol. 7, Mar. 2012, pp. 180-184.
Wu, Yu et al., "Opportunities and dilemmas of in vitro nano neural electrodes," RSC Adv., 2010, 10, 187-200.

* cited by examiner

*Primary Examiner* — Mark W. Bockelman
(74) *Attorney, Agent, or Firm* — SEYFARTH SHAW LLP

(57) ABSTRACT

A spinal sensing and stimulating device is described. The spinal sensing and stimulating device includes an electrode array, supported by a substrate. The spinal sensing and stimulating device further includes a data processing unit configured to digitize a neural signal detected from a medullary/spinal cord implant of a patient through the electrode array.

12 Claims, 15 Drawing Sheets

Current neural implants face several limitations:

- Area coverage: i.e. the brain area that controls body movement covers approximately the equivalent of half of your hand. We would require a very large implant to control a fraction of the body. A large implant causes extensive tissue damage and inflammation.

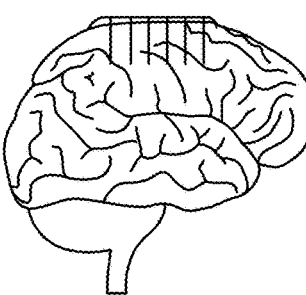

- Signal Decoding: within the brain neural signals travel in 3D and there's millions of competing synapses. Decoding such complex signals in real time is extremely difficult.

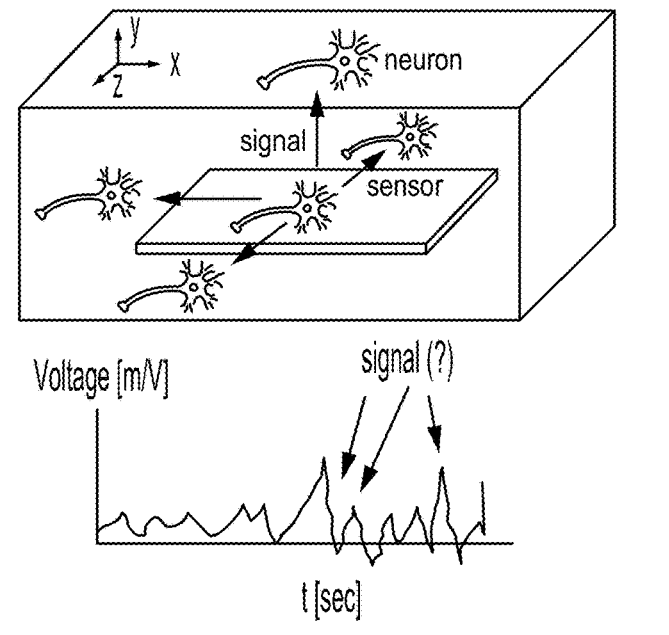

FIG. 1

OUR APPROACH: MEDULLARY/SPINAL CORD IMPLANT

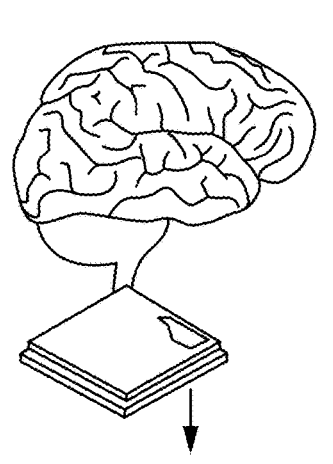

The complex neural signals in the brain get naturally decoded by the brain itself before they are sent out to the spinal cord.

-Small Area Coverage:

The white matter in the spinal cord contains a 1 to 1 map of what muscles the brain activates. The sensory section of the spinal cord also contains a map of where and what type of sensory signals is being sent to the brain. Spinal implants lead to less tissue damage and can cover the body in its entirety.

-Simple real time signal decoding:

Unlike in the brain, where signals travel in 3 dimensions and make thousands of connections with other neurons, signals within the spinal cord travel in 1 dimension and do not interact with other neurons making real-time signal interpretation exponentially easier to perform.

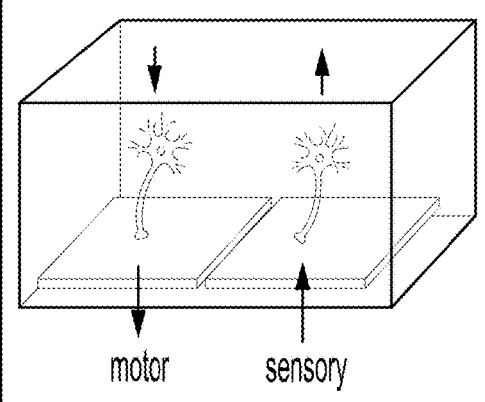

motor     sensory

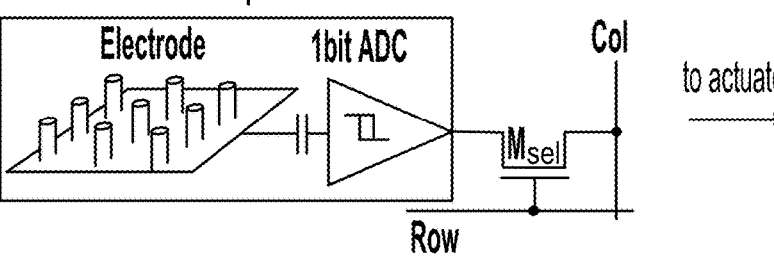

Active pixel

Electrode     1bit ADC     Col to actuators $M_{sel}$

Row

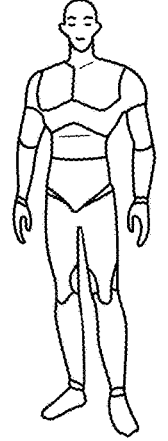

| HV | Spot | WD | Mag | HFW | |
|---|---|---|---|---|---|
| 5.0 kV | 2.0 | 18.7 mm | 150x | 1.80 mm | 1.0mm |

500

520

540

560

650

650-1

652

650-N

| HV | Spot | Det | Scan | HFW | Tilt | Mag | 2.0μm |
|---|---|---|---|---|---|---|---|
| 5.0 kV | 2.0 | ETD | 29.50 s | 5.41 μm | 37.0 ° | 50000x | Caltech |

670

670-1

| HV | Spot | Det | Scan | HFW | Tilt | Mag | ├———— 1.0μm ————┤ |
|---|---|---|---|---|---|---|---|
| 5.0 kV | 2.0 | ETD | 29.50 s | 4.51 μm | 35.5 ° | 60000x | Caltech |

What makes our platform unique?

Active pixel

Electrode    1bit ADC $M_{sel}$

Row

Col

Location:
White matter of the spinal cord or brainstem

Bi-directionality:
Our probe is capable of both sensing and stimulating neural tissue

Closed-loop:
Minimum need for patient training and compliance to use our device

In-Pixel Digitization:
Action potentials are detected and turned into a digital 1 or 0 directly on pixel which minimizes noise and power consumption.

*FIG. 8B*

Why the Spinal Cord?

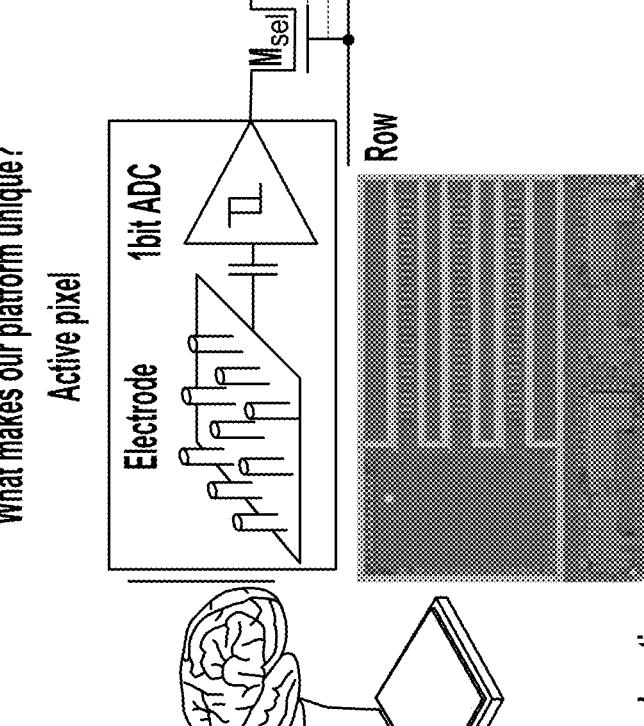

motor    sensory

Massive Signal Decoding Simplification:
1D (white matter) VS 3D signal transmission

Larger Signal to Noise ratio:
Compound Action Potentials

Small Area Coverage to Functional Coverage Ratio:
The cross sectional area of the spinal cord (~1cm²) contains the sensory and motor map of the entire body.

*FIG. 8A*

Active Pixel

940

Passive Probe

Intraspinal Stimulator 970

Bladder Sensor Readout Unit 980

$\overline{\Phi 1}$ $\Phi 1$

Sacral Nerve Stimulator 930

Power Harvesting Unit 990

ASIC

Intraspinal Sensing Chip 960

Readout

Transmit OUT 962

Subcutaneous implant (~2 mm) 915

External Unit and Power Bladder Stimulation 910

950

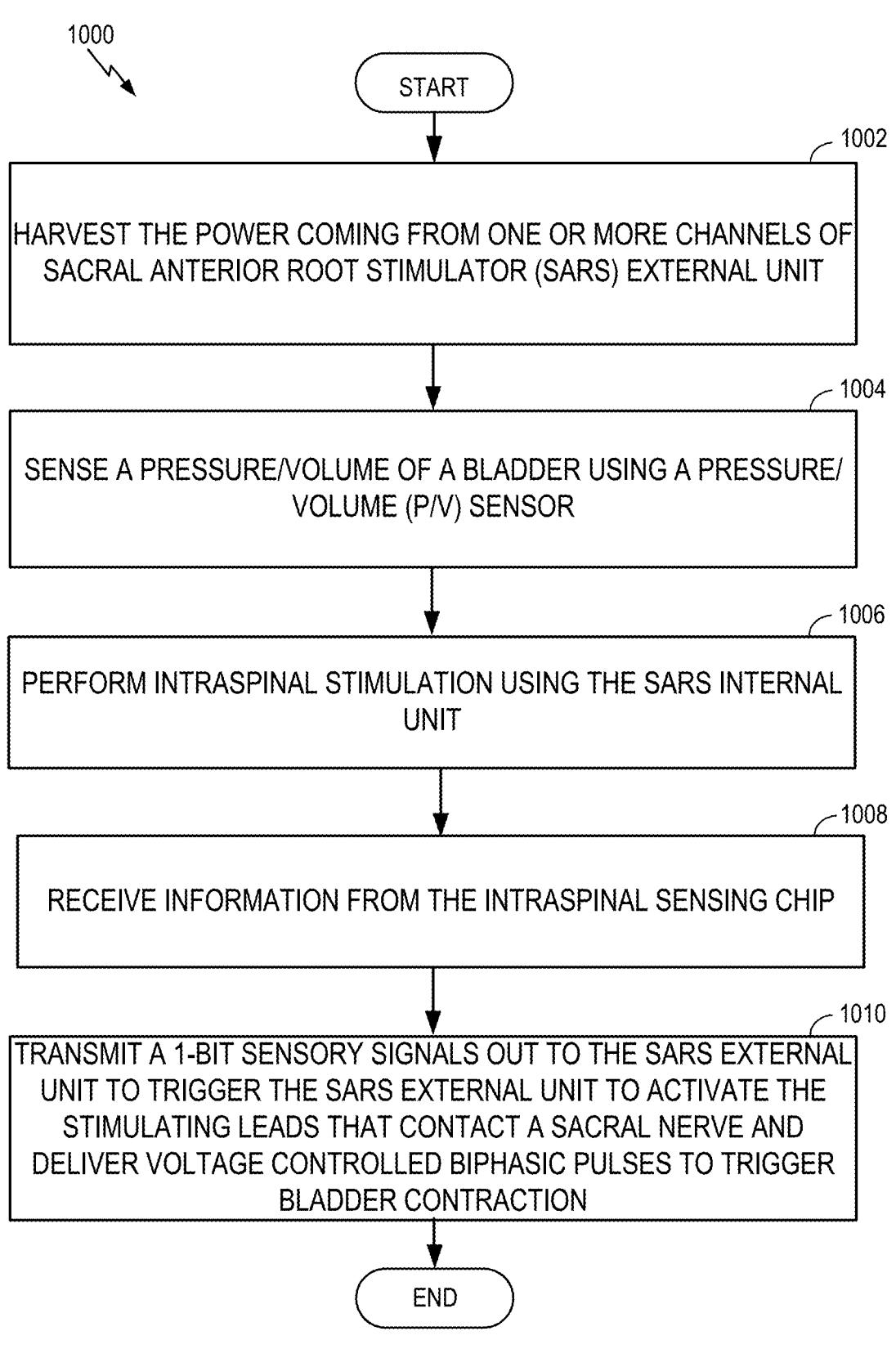

1000

START

1002

HARVEST THE POWER COMING FROM ONE OR MORE CHANNELS OF SACRAL ANTERIOR ROOT STIMULATOR (SARS) EXTERNAL UNIT

1004

SENSE A PRESSURE/VOLUME OF A BLADDER USING A PRESSURE/ VOLUME (P/V) SENSOR

1006

PERFORM INTRASPINAL STIMULATION USING THE SARS INTERNAL UNIT

1008

RECEIVE INFORMATION FROM THE INTRASPINAL SENSING CHIP

1010

TRANSMIT A 1-BIT SENSORY SIGNALS OUT TO THE SARS EXTERNAL UNIT TO TRIGGER THE SARS EXTERNAL UNIT TO ACTIVATE THE STIMULATING LEADS THAT CONTACT A SACRAL NERVE AND DELIVER VOLTAGE CONTROLLED BIPHASIC PULSES TO TRIGGER BLADDER CONTRACTION

END

*FIG. 10*

SYSTEM AND METHOD FOR IMPLANTABLE NEURAL SENSING AND STIMULATING PROBES

CROSS-REFERENCE TO RELATED APPLICATION

The present application claims the benefit of U.S. Provisional Patent Application No. 63/432,294, filed Dec. 13, 2022, and titled "SYSTEM AND METHOD FOR IMPLANTABLE NEURAL SENSING AND SIMULATING PROBES," the disclosure of which is expressly incorporated by reference herein in its entirety.

BACKGROUND

Field

Certain aspects of the present disclosure generally relate to systems and methods for implantable neural sensing and stimulating probes.

Background

Establishing reliable correlations between one's physiological signals and the associated cognitive and/or psychological states may enable valuable and desired applications for various uses. For example, potential applications include clinical trials as well as consumer electronics domains, amongst others. Such correlations, extensively explored in fundamental sciences, are the focus of various translational attempts into specialized applications such as assessment of cognitive impairment as well as enabling the physically impaired to communicate.

Several factors may be used to determine sensory and/or cognitive information about a subject. For example, such factors may include the type of physiological signals and/or behavioral responses to detect and measure, the type of stimuli to evoke the subject's response, duration of the stimuli, inter-stimuli interval, number of repetitions of each presentation of stimuli, the levels of the stimuli (e.g., sound, brightness or contrast levels, etc.), markers associated with the onset of presentation of each stimuli, etc., as well as the recording sensors and systems. Additionally, the physiological parameters of use (e.g., voltage, power, frequency, etc.), the related time window for analysis, and the analysis structure that can affect the brain signal recordings and correlated cognitive assessment are significant factors. Deviations or mistakes from one or multiples of these parameters can make the difference between a useful or an artifact driven, useless device, system, application, and/or method.

Current brain-machine interfaces (BMI) that aim to provide effective therapies for patients with paralysis mostly target the brain. Despite impressive results, such devices hit critical roadblocks that are inherent to the brain's architecture. In particular, the brain's architecture involves neurons in the cortex that form an extremely complex three-dimensional network that is partially mapped. For example, any given cortical neuron synapse is often competing with thousands of other excitatory and inhibitory neuron synapses. Due to this competitive complexity, recording from any given neuron fails to provide a sufficient, absolute value signal. As a result, a relatively large body of neurons is recorded to enable deciphering of neuronal patterns that are ultimately associated with a target behavior. Consequently, forming a behavioral-neural interface match involves significant patient participation with a medical team, which is time consuming, computationally expensive, power hungry, and heavily reliant on patient compliance.

There is a current and urgent need for a neural sensing device that can address many of these drawbacks.

SUMMARY

A spinal sensing and stimulating device is described. The spinal sensing and stimulating device includes an electrode array, supported by a substrate. The spinal sensing and stimulating device further includes a data processing unit configured to digitize a neural signal detected from a medullary/spinal cord implant of a patient through the electrode array.

A method for bladder control is described. The method includes harvesting power from one or more channels of a sacral anterior root stimulator (SARS) external unit. The method also includes sensing a pressure/volume of a bladder using a bladder volume (B/V) sensor. The method further includes performing intraspinal stimulation using a SARS internal unit. The method also includes receive information from an intraspinal sensing chip. The method further includes transmit a 1-bit sensory signals to trigger the SARS internal unit to activate stimulating leads that contact a sacral nerve and deliver voltage controlled biphasic pulses to trigger contraction of the bladder.

This has outlined, rather broadly, the features and technical advantages of the present disclosure in order that the detailed description that follows may be better understood. Additional features and advantages of the present disclosure is described below. It should be appreciated by those skilled in the art that this present disclosure may be readily utilized as a basis for modifying or designing other structures for carrying out the same purposes of the present disclosure. It should also be realized by those skilled in the art that such equivalent constructions do not depart from the teachings of the present disclosure as set forth in the appended claims. The novel features, which are believed to be characteristic of the present disclosure, both as to its organization and method of operation, together with further objects and advantages, will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding of the present disclosure, reference is now made to the following description taken in conjunction with the accompanying drawings.

FIG. 1 shows a conventional neural implant, which suffers from several limitations, including area coverage and signal decoding.

FIG. 2 shows a medullary/spinal cord implant, according to aspects of the present disclosure.

FIGS. 8A and 8B illustrate advantages of a medullary/spinal cord implant using the disclosed spinal sensing device, according to certain aspects of the disclosed technology.

FIG. 10 is a flowchart illustrating a bladder control scheme process, according to aspects of the present disclosure.

DETAILED DESCRIPTION

Figure 3:
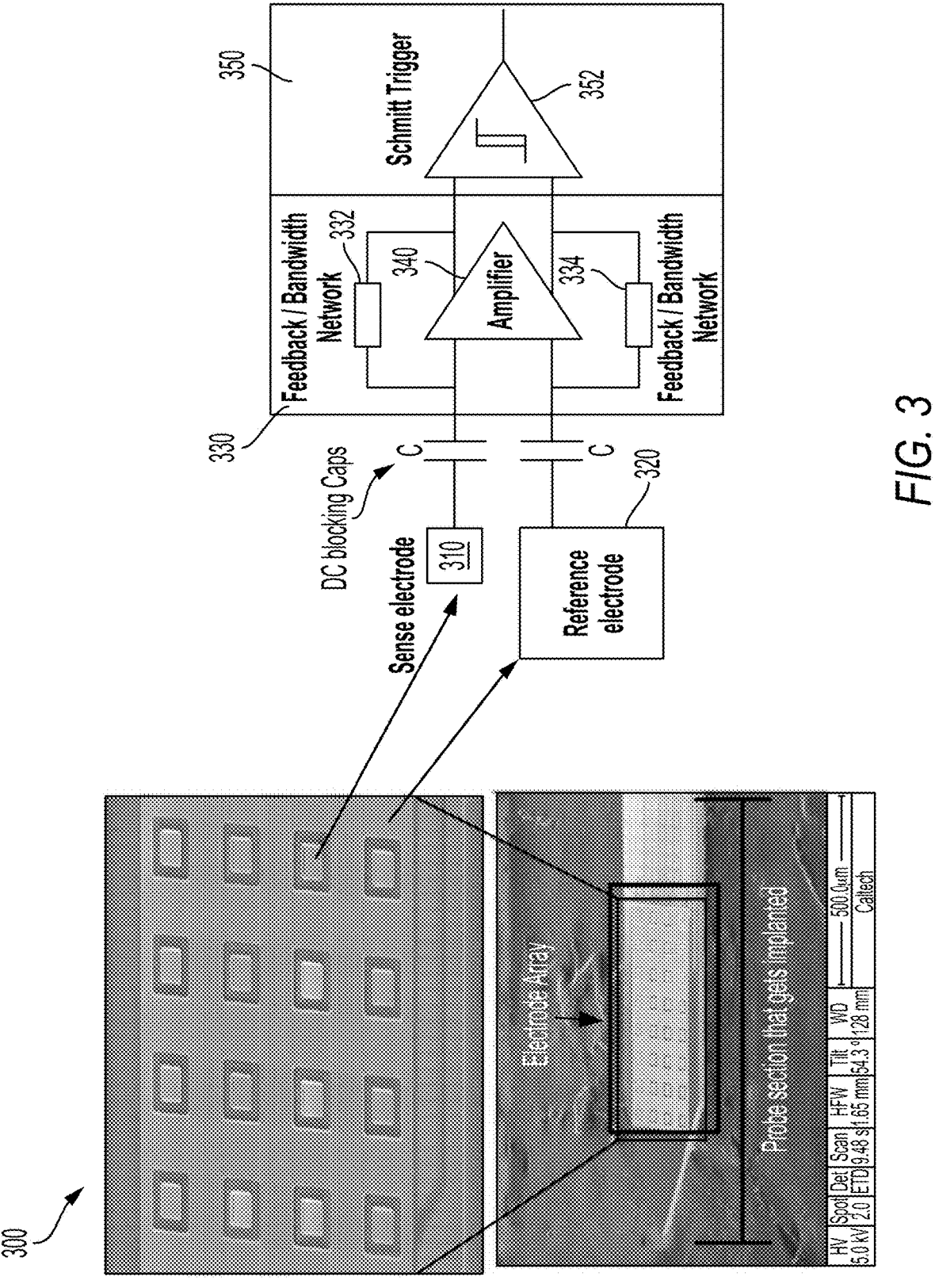
FIG. 3 illustrates the design and fabrication of a spinal sensing device, having implantable sensing electrodes, according to aspects of the present disclosure.

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. It will be apparent, however, to those skilled in the art that these concepts may be practiced without these specific details. In some instances, well-known structures and components are shown in block diagram form in order to avoid obscuring such concepts.

As described herein, the use of the term "and/or" is intended to represent an "inclusive OR," and the use of the term "or" is intended to represent an "exclusive OR." As described herein, the term "exemplary" used throughout this description means "serving as an example, instance, or illustration," and should not necessarily be construed as preferred or advantageous over other exemplary configurations. The term "coupled" used throughout this description means "connected, whether directly or indirectly through intervening connections (e.g., a switch), electrical, mechanical, or otherwise," and is not necessarily limited to physical connections. Additionally, the connections can be such that the objects are permanently connected or releasably connected. The connections can be through switches.

Current brain-machine interfaces (BMIs) that aim to provide effective therapies for patients with paralysis mostly target the brain. Despite impressive results, such devices hit critical roadblocks that are inherent to the brain's architecture. In particular, the brain's architecture involves neurons in the cortex that form an extremely complex three-dimensional network that is only partially mapped. For example, any given cortical neuron synapse is often competing with thousands of other excitatory and inhibitory neuron synapses. Due to this competitive complexity, recording from any given neuron fails to provide a sufficient, absolute value signal. As a result, a relatively large body of neurons is recorded to enable deciphering of neuronal patterns that are ultimately associated with a target behavior. Consequently, forming a behavioral-neural interface match involves high electrode density and computationally expensive, power-hungry electrical interfaces, involving significant patient participation with the training medical team, which is time consuming and heavily reliant on patient compliance.

By contrast, with the three-dimensionality of cortical neurons, spinal cord communication happens in one-dimension (e.g., up/down) and is discrete (e.g., no competing synapses within the white matter). In particular, white matter of the spinal cord is mostly composed of a set of one-way channels that connect the brain and periphery, which makes movement and sensation possible. The major carriers of motor and sensory information in the spinal cord are axon bundles, which are organized in tracts that form a regional map of the body. For example, pressure applied to the big toe is relayed to the brain via a medial region of the fasciculus gracilis, while motion of the shoulder is localized in the medial region of the lateral cortico-spinal tract. As a result of this intrinsic map provided by the spinal cord, signal decoding becomes drastically easier than in the cerebral cortex, leading to minimal patient-interface training, which greatly simplifies the adoption of spinal interfaces.

Some aspects of the present disclosure relate to the design and fabrication of a spinal sensing device, having implantable sensing and neural stimulating probes. In some aspects of the present disclosure, the probes are provided in a single or multiple shank configuration and adapted for implanting in the spinal cord or brainstem of a patient. In this arrangement, the probes record from and stimulate axons that reside in the white matter of these anatomical regions (e.g., the spinal cord or brainstem). In operation, the probes are operated (1) to detect action potentials: (2) binarize the detected action potentials into a digital 1 or 0: (3) suppress local field potentials; and (4) stimulate axons within the white matter spinal cord or brainstem to evoke action potentials.

In some aspects of the present disclosure, the probes include a sensing/stimulating section, which is referred to as an "electrode array" that is composed of a number of individual electrodes ranging from 1 to 1044. These electrodes may be protruding, flat, or patterned. Additionally, the patterned electrodes are composed of either nanopillars (e.g., ranging in diameter from 60-500 nanometers with a height ranging from 1.5-8 microns), or micropillars (e.g., ranging in diameter from 1.5-5 microns with a height ranging from 20-100 microns). Either type of electrode, flat or patterned, may be coated with a conductive material including, but not limited to, platinum (Pt), titanium nitride (TiN), iridium (Ir), or iridium oxide ($IrO_x$). In some configurations, the pillars, either nanopillars or micropillars, may have an insulated bottom portion, which improves confinement of the electric potential. In some aspects of the present disclosure, an integrated "internal" reference is patterned next to the sensing/stimulating electrodes, which significantly suppress local field potentials and drastically decrease DC voltage drift.

Additionally, the probes may be passive (e.g., the sensing and stimulating probe is physically separate from the integrated circuit) or active (e.g., the electrode, whether protruding, flat, or patterned on the integrated circuit). An active sensing probe features active pixel technology. For example, in an active sensing probe, each electrode (e.g., pixel) contains a differential amplifier and a comparator, which digitize a detected action potential into a 1-bit (1 or 0) signal. This active sensing probe architecture is drastically different from current active pixel complementary metal-oxide-semiconductor (CMOS) probes, which digitizes the entire action potential waveform.

FIG. 1 shows a conventional neural implant, which suffers from several limitations, including area coverage and signal decoding. Current brain-machine interfaces (BMI) that aim to provide effective therapies for patients with paralysis generally target the brain. Despite impressive results, such devices hit critical roadblocks that are inherent to the brain's architecture. As shown in FIG. 1, the brain's architecture involves neurons in the cortex that form an extremely complex three-dimensional network that is only partially mapped. For example, any given cortical neuron synapse is often competing with thousands of other excitatory and inhibitory neuron synapses. Due to this competitive complexity, recording from any given neuron fails to provide a sufficient, absolute value signal, as shown in FIG. 1. As a result, a relatively large body of neurons is conventionally recorded to enable deciphering of neuronal patterns that are ultimately associated with a target behavior. Consequently, forming a behavioral-neural interface match involves high electrode density, and computationally expensive, power-hungry electrical interfaces, involving significant patient participation with the training medical team, which is time consuming and heavily reliant on patient compliance.

FIG. 2 shows a medullary/spinal cord implant, according to aspects of the present disclosure. By contrast, with the three-dimensionality of cortical neurons, spinal cord communication happens in one-dimension (e.g., up/down) and is discrete (e.g., no competing synapses within the white matter). In particular, white matter of the spinal cord is mostly composed of a set of one-way channels that connect the brain and periphery, which makes movement and sensation possible. The major carriers of motor and sensory information in the spinal cord are axon bundles. These axon bundles are organized by the body in tracts that form a regional map of the body. For example, pressure applied to the big toe is relayed by the body to the brain via a medial region of the fasciculus gracilis, while motion of the shoulder is localized in the medial region of the lateral cortico-spinal tract. As a result of this intrinsic map provided by the spinal cord, signal decoding becomes drastically easier than in the cerebral cortex, leading to minimal patient-interface training, which greatly simplifies the adoption of spinal interfaces.

FIG. 3 illustrates the design and fabrication of a spinal sensing device, having implantable sensing electrodes of the spinal sensing device, according to aspects of the present disclosure. In some aspects of the present disclosure, the probes of the spinal sensing device are provided in a single or multiple shank configuration and adapted for implanting in the spinal cord or brainstem of a patient. In this arrangement, the probes record from and stimulate axons that reside in the white matter of these anatomical regions (e.g., the spinal cord or brainstem). In operation, the probes are operated (1) to detect action potentials: (2) binarize the detected action potentials into a digital 1 or 0: (3) suppress local field potentials; and (4) stimulate axons within the white matter spinal cord or brainstem to evoke action potentials.

As shown in FIG. 3, a spinal sensing device 300 is composed of sensing electrodes 310, which may be patterned (e.g., micropillars or nanopillars) or flat. In some aspects of the present disclosure, the probes of the spinal sensing device 300 include a sensing/stimulating section, which is referred to as an electrode array that is composed of a number of individual ones of the sensing electrodes 310, ranging from 1 to 1044. These sensing electrodes 310 may be protruding, flat, or patterned. In some aspects of the present disclosure, the patterned electrodes are composed of either nanopillars (e.g., ranging in diameter from 60-500 nanometers with a height ranging from 1.5-8 microns) or micropillars (e.g., ranging in diameter from 1.5-5 microns with a height ranging from 20-100 microns). Either type of electrode, flat or patterned, may be coated with a conductive material including, but not limited to, platinum (Pt), titanium nitride (TiN), iridium (Ir), or iridium oxide (IrO$_x$). In some configurations, the pillars, either nanopillars or micropillars, may have an insulated bottom portion, which improves confinement of the electric potential.

As further illustrated in FIG. 3, the spinal sensing device 300 includes an internal reference electrode 320, which is patterned proximate the sensing electrodes 310. In some designs, the internal reference electrode 320 is sized (e.g., ten (10) times) larger than the sensing electrodes 310 to maintain a low impedance, which is important for adequate reference performance. The integrated, internal reference electrode 320 is patterned next to the sensing electrodes 310, which significantly suppress local field potentials and drastically decrease DC voltage drift. Additionally, the probes may be passive (e.g., the sensing and stimulating probe is physically separate from the integrated circuit) or active (e.g., the electrode, whether protruding, flat, or patterned, is processed on the integrated circuit).

As shown in FIG. 3, the spinal sensing device 300 includes passive sensing probes, according to aspects of the present disclosure. For example, in a passive sensing probe, each of the sensing electrodes 310 has separate differential amplifiers and a comparator off probe, which digitize a detected action potential into a 1-bit (1 or 0) signal. This passive sensing probe architecture is drastically different from current implementations, in which an entire action potential waveform in digitized. In this example, the sensing electrodes 310 and the internal reference electrode 320 are coupled to DC blocking capacitors (C). The DC blocking capacitors C are provided to (1) avoid amplification of a DC offset between the sensing electrodes 310 and the internal reference electrode 320, and (2) to reject local field potentials (LFPs).

In this configuration, an amplification stage 330 of the spinal sensing device 300 includes feedback/bandwidth network paths 332 and 334, as well as an amplifier 340 coupled to the DC blocking capacitors C. In this example, the amplifier 340 receives a neural signal from the sensing electrodes 310 and the internal reference electrode 320 and amplifies the neural signal to a minimum level of a predetermined signal to noise ratio (SNR) level (e.g., a minimum of 20 dB min). In operation, the differential signal is provided to a comparator stage 350, which includes an analog to digital converter (ADC) 352 for converting the differential signal into a digital signal.

As described, the combination of the DC blocking capacitors C, the amplification stage 330 and the comparator stage 350 provide a data processing unit. In addition, feedback/bandwidth network paths 332 and 334 set a desired gain and provide filtering of unwanted frequencies. For example, the spinal sensing device 300 may be configured with a narrow bandwidth (e.g., 500-1800 Hz). The spinal sensing device 300, using the data processing unit, may determine a mental state of the patient according to a neural signal detected from the patient.

As further illustrated in FIG. 3, amplified analog signals from the amplifier 340 are provided to the comparator stage 350. In this example, the comparator stage 350 is implemented using a one-bit analog to digital converter (ADC) device 352 (e.g., a Schmitt trigger). In operation, the ADC device 352 receives the amplified analog neural signal from the amplifier 340 and compares the signal to a programmable threshold. When the signal crosses the programmable threshold, a digital value in the form of (1) or (0) is output from the 1-bit ADC device 352 (as in the case of an action potential). In case the comparator stage 350 is set up as non-inverting, when an action potential occurs, the incoming signal will dip below a pre-programmed threshold and the comparator stage 350 outputs a digital zero (0). By contrast, when no action potential is present, the incoming signal is larger than the threshold voltage and the output of the comparator stage 350 is a digital one (1). In case the comparator stage 350 is set up as inverting, the opposite occurs.

In some aspects of the present disclosure, the DC blocking capacitors C, the amplifier 340, and the ADC device 352 are fabricated below the sensing electrodes 310, in a complementary metal-oxide-semiconductor (CMOS) active probe configuration. In an alternative configuration, the DC blocking capacitors C, the amplifier 340, and the ADC device 352 are fabricated in a separate block and wire bonded to a passive electrode array. The internal reference electrode 320 is shared among an electrode array block, which may be composed of a predetermined number of electrodes (e.g., 4, 8, 16, 32, etc.).

Figure 4:
FIG. 4 illustrates the design and fabrication of a spinal sensing device, having active sensing electrodes, according to aspects of the present disclosure.

FIG. 4 illustrates the design and fabrication of a spinal sensing device, having implantable sensing and neural stimulating probes, according to aspects of the present disclosure. As shown in FIG. 4, the spinal sensing device 400 includes active sensing probes, featuring active pixel technology. For example, in an active sensing probe, each of the sensing electrodes 410 (e.g., pixel) contains a differential amplifier and a comparator to provide an analog to digital converter (ADC) 450, which digitizes a detected action potential into a binary (e.g., 1 or 0) signal. This active sensing probe architecture is drastically different from current active pixel complementary metal-oxide-semiconductor (CMOS) probes, in which an entire action potential waveform is digitized.

Figure 5A:
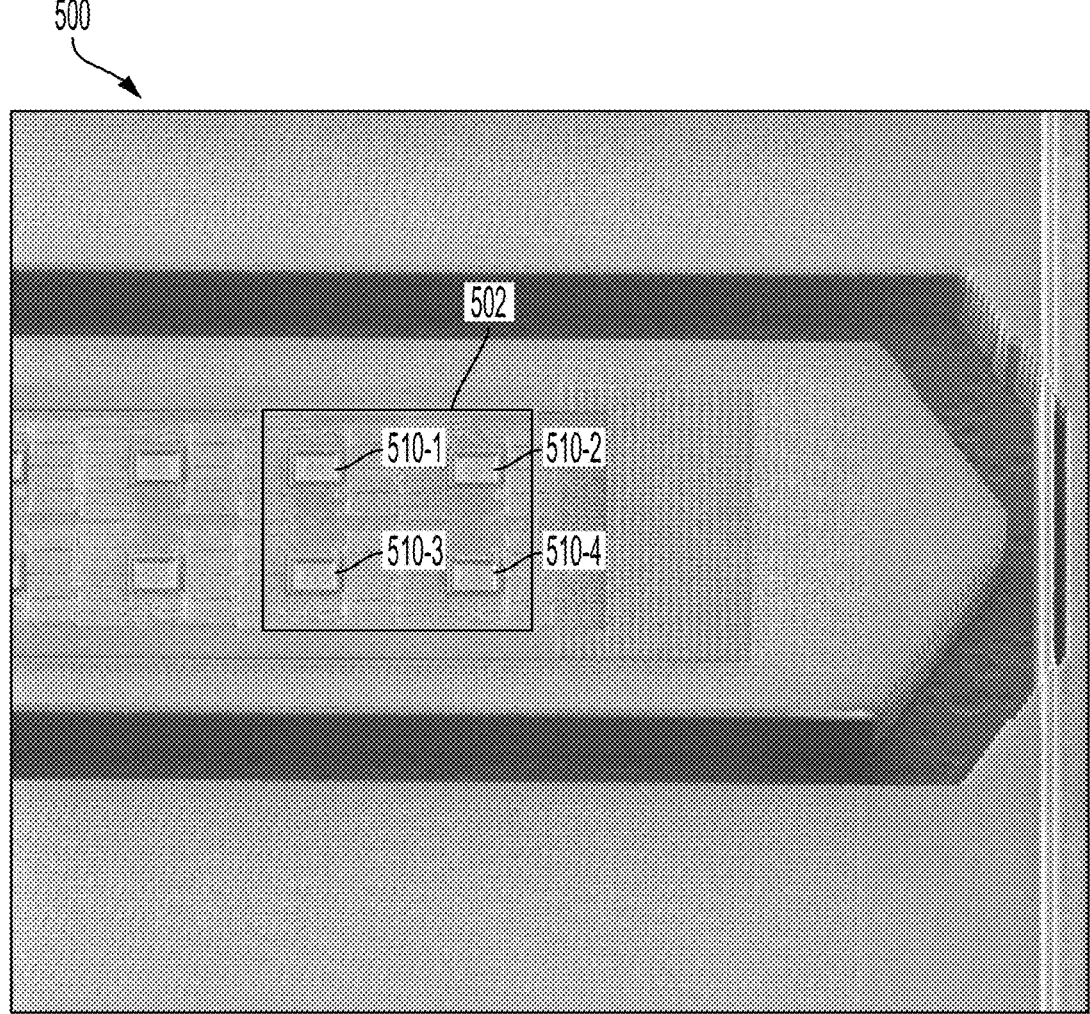
FIGS. 5A-5D illustrate the design and fabrication of a spinal sensing device, having implantable sensing and neural stimulating probes, according to aspects of the present disclosure.

FIGS. 5A-5D illustrates the design and fabrication of a spinal sensing device, having implantable sensing and neural stimulating probes, according to aspects of the present disclosure. FIG. 5A illustrates a top view of a spinal sensing device 500, showing a highlighted portion 502 of implantable sensing and neural stimulating probes, according to aspects of the present disclosure. As shown in FIG. 5A, the spinal sensing device 500 includes protruding sensing electrodes 510 (e.g., 510-1, 510-2, 510-3, 510-4), that may rely on a separate differential amplifier and a comparator to provide an analog to digital converter (ADC), which digitizes a detected action potential into a binary (e.g., 1 or 0) signal. This spinal sensing device 500 is also different from current active pixel complementary metal-oxide-semiconductor (CMOS) probes, in which an entire action potential waveform is digitized.

Figure 5B:
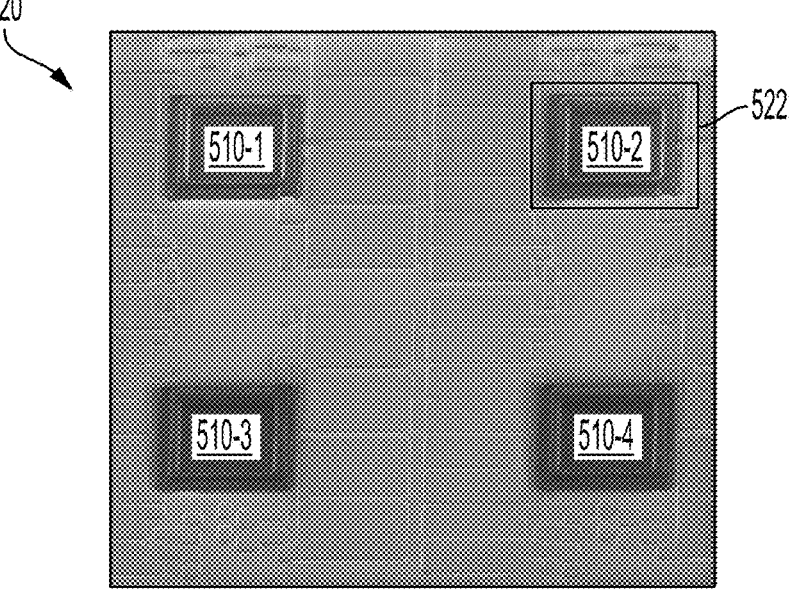

FIG. 5B further illustrates an exploded view 520 of the highlighted portion 502 of the spinal sensing device 500 of FIG. 5A, according to aspects of the present disclosure. In this example, the protruding sensing electrodes 510 (510-1, 510-2, 510-3, 510-4) are further illustrated, in which a highlighted portion 522 surrounds a second protruding sensing electrode 510-2.

Figure 5C:
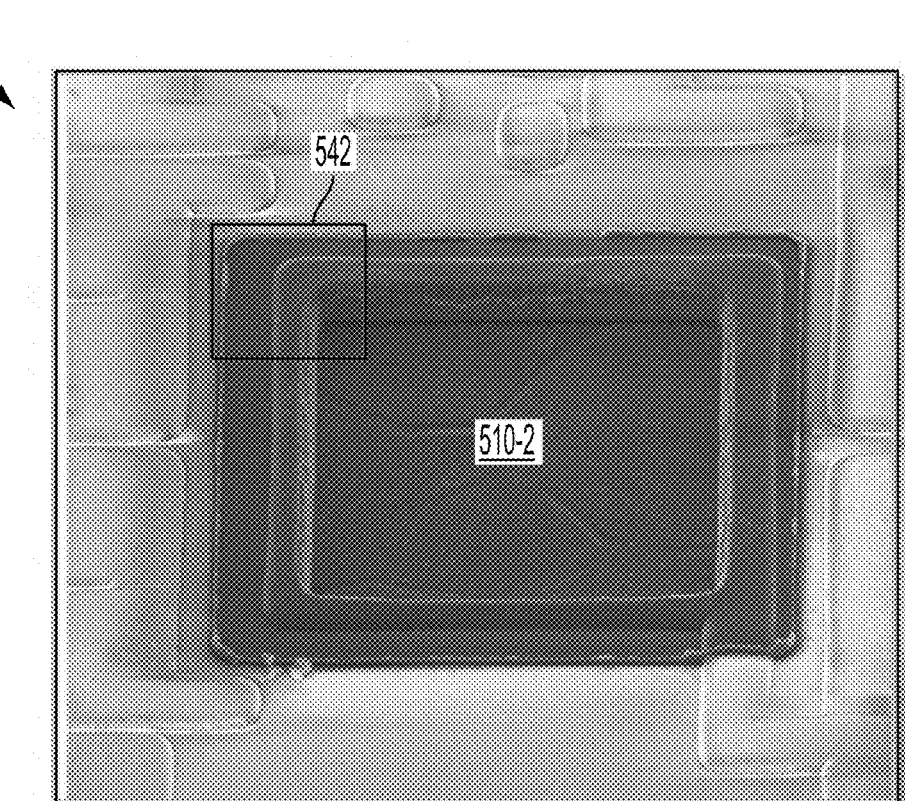

FIG. 5C further illustrates an exploded view 540 of the highlighted portion 522 of the second protruding sensing electrode 510-2 of FIG. 5B, according to aspects of the present disclosure. In this example, the second protruding sensing electrode 510-2 is further illustrated, in which a highlighted portion 542 surrounds a corner of the second protruding sensing electrode 510-2.

Figure 5D:
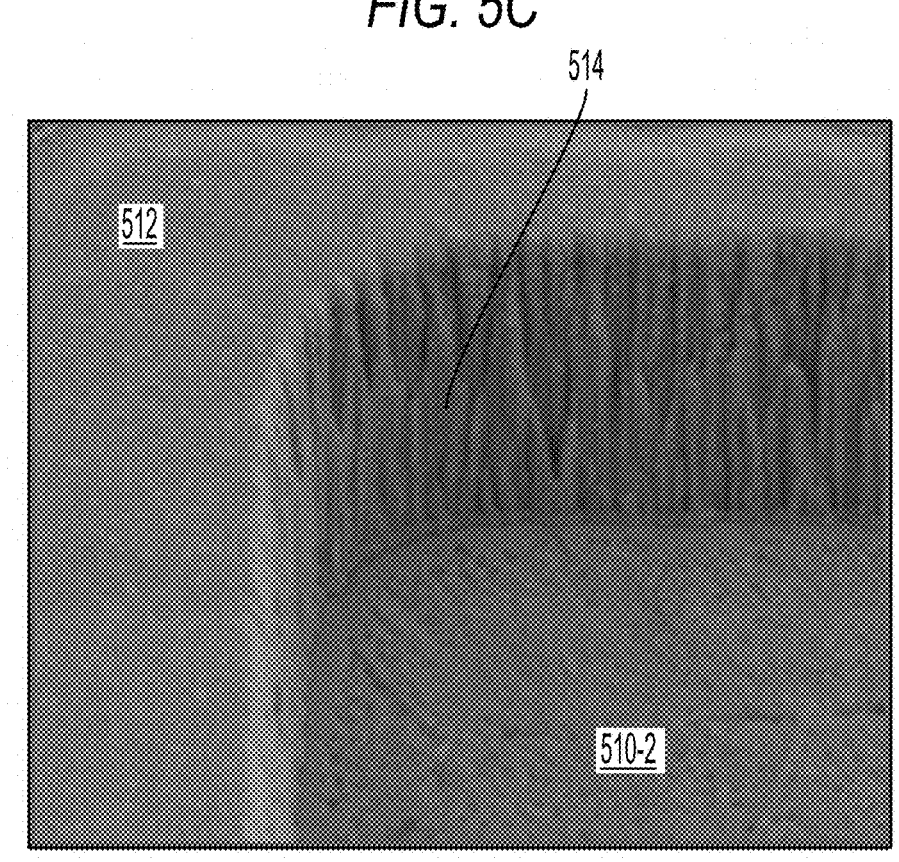

FIG. 5D further illustrates an exploded view 560 of the highlighted portion 542 of the second protruding sensing electrode 510-2 of FIG. 5C, according to aspects of the present disclosure. In this example, a ridge 512 of the second protruding sensing electrode 510-2 is further illustrated, in which a sidewall of the ridge 512 of the second protruding sensing electrode 510-2 includes cracks 514. These cracks 514 in the ridge 512 of the second protruding sensing electrode 510-2 is caused by conventional depositing techniques of evaporation of platinum (Pt) over the second protruding sensing electrode 510-2. This conventional technique causes the cracks 514 in the ridge 512, which may lead to aluminum (Al) exposed to biological tissue, which is toxic and leads to erosion over time. In some aspects of the present disclosure, a highly conformal, low stress Pt sputtering process is performed to coat the second protruding sensing electrode 510-2 for preventing the cracks 514 on the ridge 512.

Figure 6A:
FIGS. 6A-6D are diagrams illustrating stimulating electrodes of a spinal stimulation device, according to aspects of the present disclosure.

FIGS. 6A-6D are diagrams illustrating stimulating electrodes of a spinal stimulation device, according to aspects of the present disclosure. FIG. 6A illustrates stimulating electrodes 610 (610-1, 610-2, 610-3, 610-4) of a spinal stimulation device 600, according to aspects of the present disclosure. In some aspects of the present disclosure, the stimulating electrodes 610 (610-1, 610-2, 610-3, 610-4) may be implemented as nanopatterned stimulation electrodes or micropatterned stimulation electrodes that may provide stimulation to a patient during a stimulation stage.

In some aspects of the present disclosure, the patterned electrodes are composed of either nanopillars (e.g., ranging in diameter from 60-500 nanometers with a height ranging from 1.5-8 microns), or micropillars (e.g., ranging in diameter from 1.5-5 microns with a height ranging from 20-100 microns). Either type of electrode, flat or patterned, may be coated with a conductive material including, but not limited to, platinum (Pt), titanium nitride (TiN), iridium (Ir), or iridium oxide ($IrO_x$). In some configurations, the pillars, either nanopillars or micropillars, may have an insulated bottom portion, which improves confinement of the electric potential, for example, as shown in FIG. 6D.

Figure 6B:
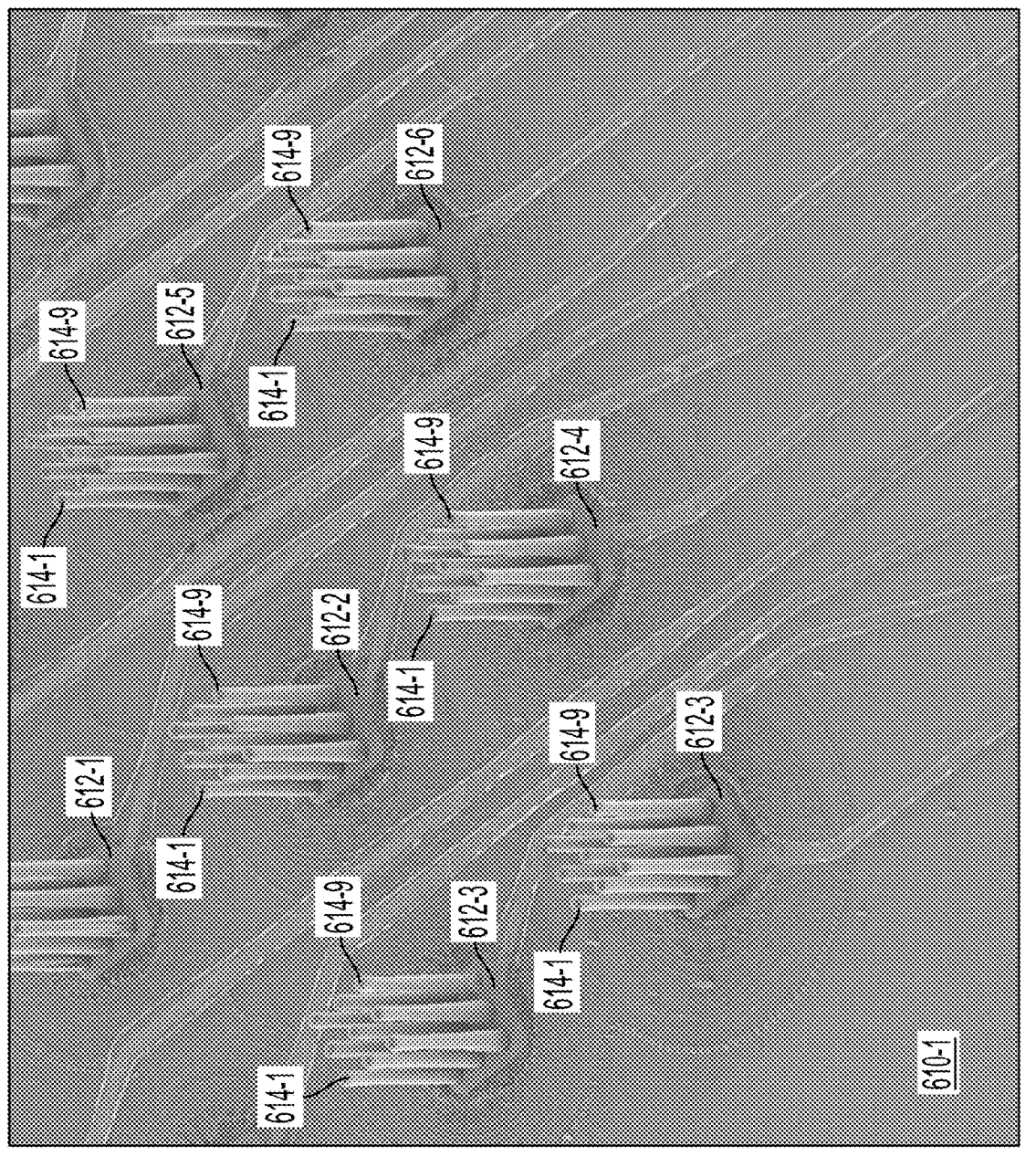

FIG. 6B illustrates an array of pillar-patterned stimulation electrodes 612 (e.g., 612-1, 612-2, 612-3, 612-4, 612-5, 612-6) used to form the first stimulation electrode 610-1 of FIG. 6A, according to aspects of the present disclosure. In this example, each of the pillar-patterned stimulation electrodes 612 includes micropillars 614 (614-1, . . . , 614-9). The micropillars 614 exponentially increase a surface area of the first stimulation electrode 610-1. In operation, the higher surface area provided by the micropillars 614 results in increased capacitance, such that for a given voltage, the charge injection (Q) is higher. Consequently, a stimulation stage of the spinal stimulation device 600 may be configured according to a voltage-controlled stimulation scheme or a current controlled stimulation scheme for operating the array of pillar-patterned stimulation electrodes 612.

Figure 6C:
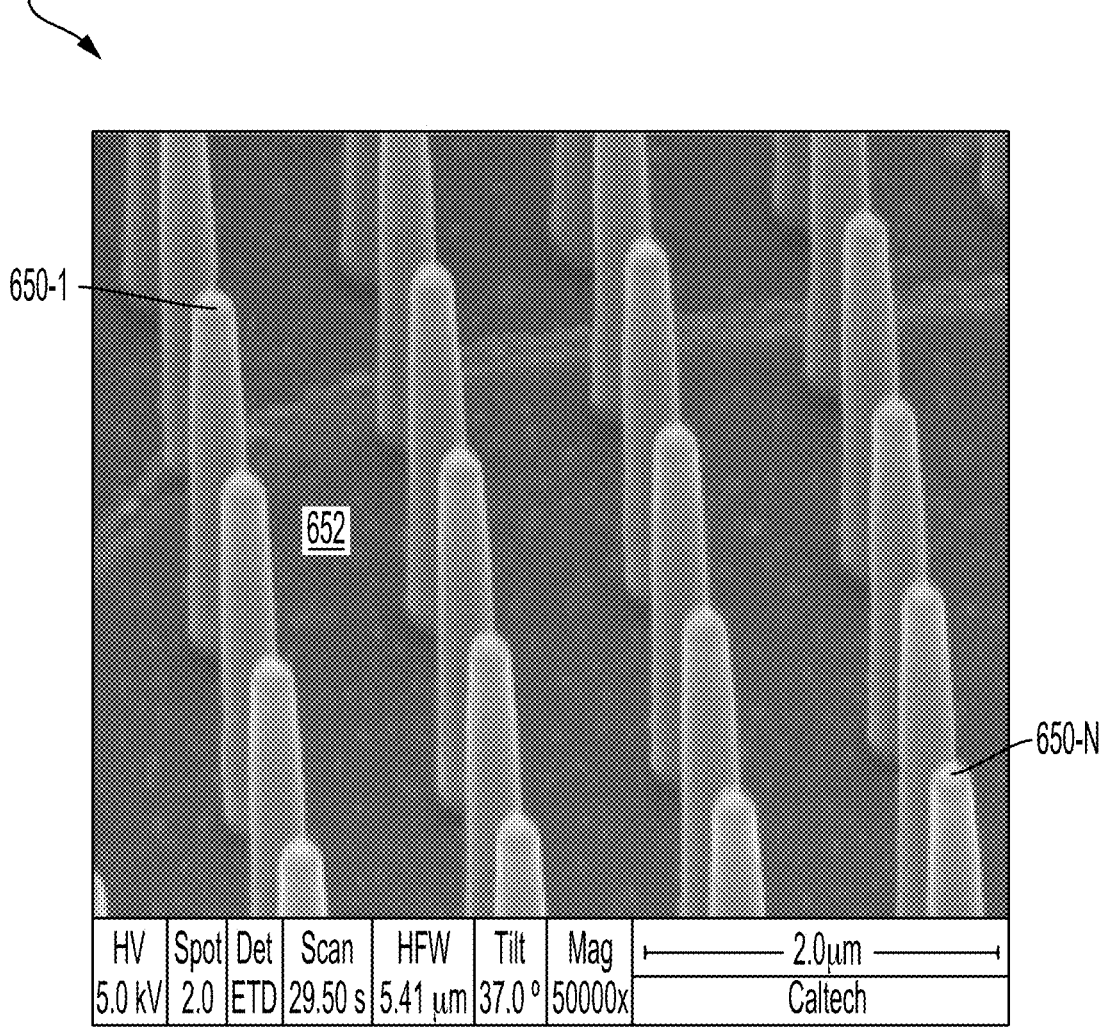
Figure 6D:
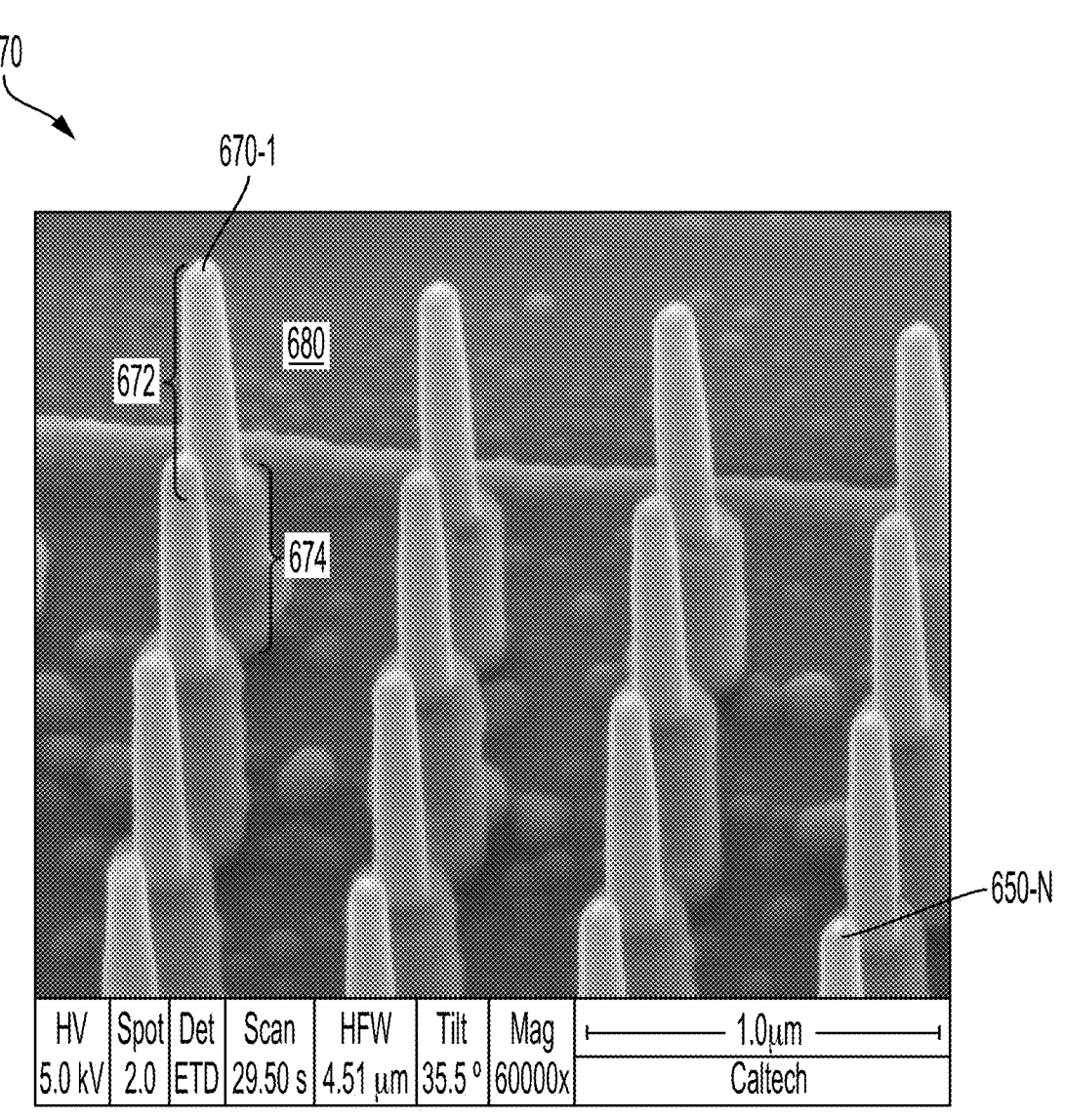

FIGS. 6C and 6D illustrate an array of pillars on substrates, according to aspects of the present disclosure. As shown in FIG. 6C, an array of pillars 650 (e.g., 650-1, . . . , 650-N) are formed on a substrate 652, which may be used to form the first stimulation electrode 610-1 of FIG. 6A, according to aspects of the present disclosure. In this example, both the substrate 652 and each of the pillars 650 are conductive. As shown in FIG. 6D, an array of pillars 670 (e.g., 670-1, . . . , 670-N) is formed on a substrate 680, which may be used to form the first stimulation electrode 610-1 of FIG. 6A, according to aspects of the present disclosure. In this example, each of the pillars 670 includes a conductive portion 672 and a non-conductive portion 674. In this aspect of the present disclosure, both the substrate 680 and the non-conductive portion 674 of the pillars 650 are nonconductive.

Figure 7:
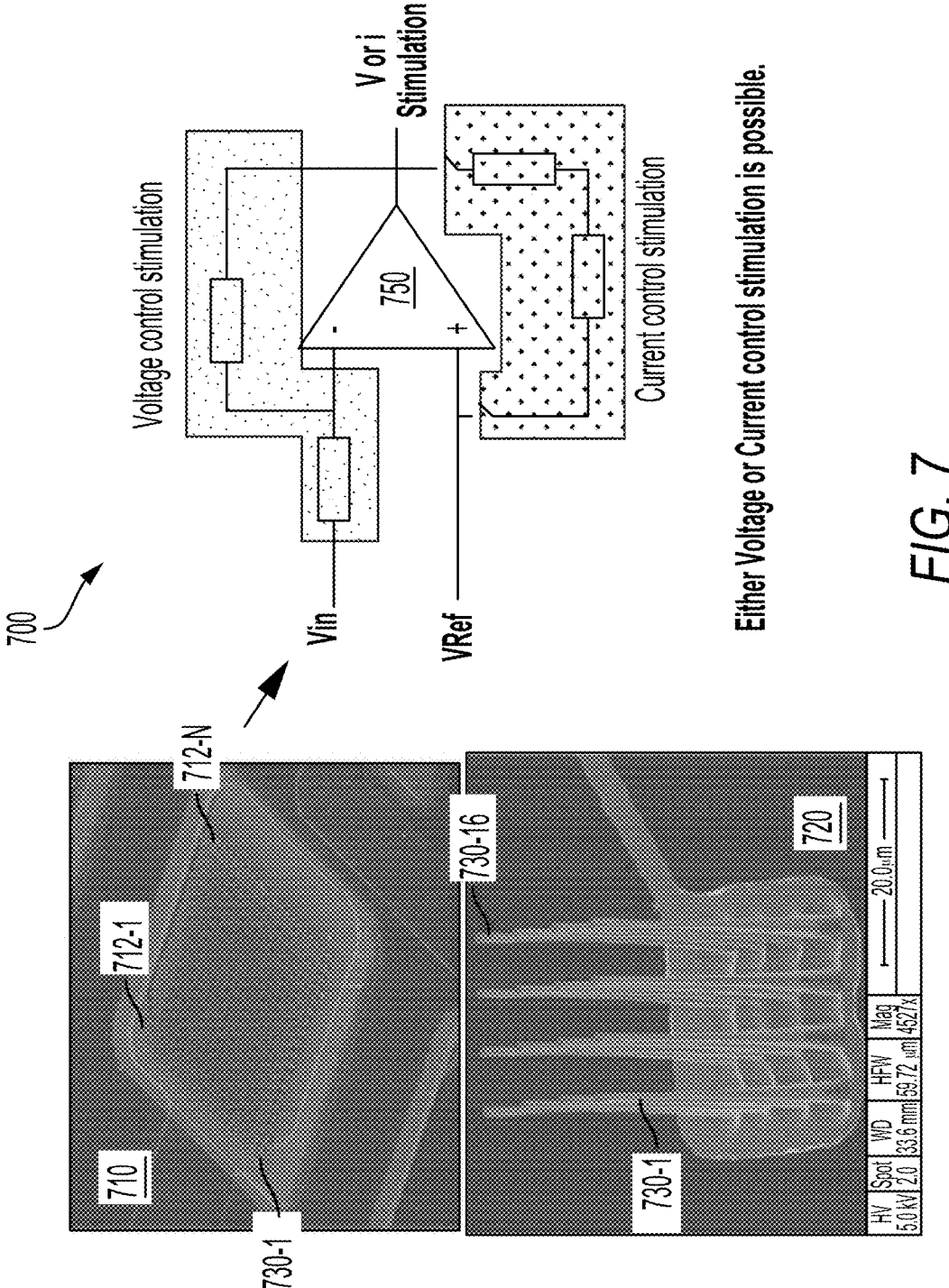
FIG. 7 is a block diagram further illustrating stimulating electrodes and a stimulation stage of a spinal stimulation device, according to aspects of the present disclosure.

FIG. 7 is a block diagram further illustrating stimulating electrodes and a stimulation stage of a spinal stimulation device 700, according to aspects of the present disclosure. FIG. 7 illustrates a nanopatterned stimulation electrode 710 and a micropatterned stimulation electrode 720 that may provide stimulation to a patient, as directed by a stimulation stage 750. In this example, the nanopatterned stimulation electrode 710 includes nanopillars 712 (712-1, . . . , 712-N). The nanopillars 712 exponentially increase a surface area of the nanopatterned stimulation electrode 710. In operation, the higher surface area provided by the nanopillars 712 also results in increased capacitance, such that for a given voltage, the charge injection (Q) is higher. Consequently, the stimulation stage 750 of the spinal stimulation device 700 may be configured according to a voltage-controlled stimulation scheme or a current controlled stimulation scheme for operating the nanopatterned stimulation electrode 710.

In this example, the micropatterned stimulation electrode 720 includes micropillars 730 (730-1, 730-16). The micropillars 730 also exponentially increase a surface area of the micropatterned stimulation electrode 720. In operation, the higher surface area provided by the micropillars 730 also results in increased capacitance, such that for a given voltage, the charge injection (Q) is higher. Consequently, the stimulation stage 750 of the spinal stimulation device 700 may be configured according to a voltage-controlled stimulation scheme or a current controlled stimulation scheme for operating the micropatterned stimulation electrode 720.

In some aspects of the present disclosure, the nanopatterned stimulation electrode 710 and/or the micropatterned stimulation electrode 720 may operate using a lower voltage or current pulse compared to standard thresholds for flat electrodes, which results in lower power consumption. The lower voltage or current pulse for operating the nanopatterned stimulation electrode 710 and/or the micropatterned stimulation electrode 720 is achieved due to the higher capacitance provided by the added surface area provided by the nanopillars 712 and/or the micropillars 730. Additionally, the reduced voltage/current pulse decreases the possibility of causing electrochemical reactions at the electrode-tissue interface, and the reduced power/current pulse lowers tissue heating, which decreases the possibility of causing neural tissue damage.

FIGS. 8A and 8B illustrate advantages of a medullary/spinal cord implant using the disclosed spinal sensing and stimulating device, according to certain aspects of the disclosed technology. As shown in FIG. 8A, advantages of the sensing probe architecture include an exponentially reduced transfer of information, which makes the disclosed sensing probes more amenable to real-time information processing. In particular, sending out binary information is amenable to several data compression techniques such as delta compression, which leads to a significant decrease in power consumption and data transfer rate.

For example, a massive signal decoding simplification is enabled by the disclosed sensing probe due to the one-dimension of white matter versus 3D signal transmission for decoding sensed brain signal. In particular, currently, available active neural probes sample signals at 10-20 KHz with 10-bit resolution, which is essential to re-construct the spiking waveform. The signal reconstruction process leads to limitations in the maximum number of channels that may be simultaneously read-out. For example, in an average analog to digital converter (ADC) of 10 bits, a data transfer rate of 10 bits×30 kS/s=300 kb/s per channel is provided, while the disclosed probe transfers 1 bit×10 kS/s=10 kS/s per channel, which is a thirty times (30×) reduction in data rate transmission. Additionally, the introduction of nanopillars and/or micropillars for stimulation increases the electrode charge density, which lowers the pulse voltage. Beneficially, the use of the nanopillars and/or micropillars shortens the pulse, which leads to less power dissipation as well as less heating to the tissue, meaning less possible damage to the surrounding tissue of the patient.

In addition to simpler decoding, signaling within the white matter of the spinal cord yields a significantly larger signal to noise ratio (SNR), which is important to making a faster, low power neural interface. In operation, a single axon's action potential yields extremely small amplitudes on the order of approximately 30 µV, which are challenging to detect; however, axon bundles in the spinal cord that carry information related to a given body region tend to fire all together, which are referred to as compound action potentials (CAPs). Such CAPs are a result of the summation of hundreds of single action potentials leading to spike recordings on the order of ~1 mV (SNR ~40 dB).

By comparison, cortical interfaces that aim to record from single neurons and tweeze out the spatio-temporal pathways of such signaling yield signal amplitude recordings as significant as ~200 µV with a SNR of ~26 dB. Furthermore, information condensation within the spinal cord is exponentially larger than that of the brain. Additionally, a cross-sectional area of the spinal cord at the lumbar level is ~1 $cm^2$, half of which is composed of white matter. In other words, the entire sensory and motor information between the brain and the lower half of the body is mapped out over an area of approximately 0.5 $cm^2$, while the somatosensory and motor areas in the cortex cover approximately 400 $cm^2$.

As noted in FIG. 6B, the compression of information in the spinal cord enables the use of a much smaller invasive neural probe to more effectively and reproducibly communicate with a larger, more specific portion of the body, which leads to much lower risks of infection and inflammation in patients. Additionally, the disclosed neural probe is bi-directional, which provides the capability of both sensing and stimulating neural tissue. The disclosed neural sensing probe also provides a closed-loop solution, which involves a minimum amount of patient training and compliance for effectively using the disclosed sensing device. In some aspects of the present disclosure, the disclosed sensing device provides in-pixel digitization. As described herein, in-pixel digitization refers to the detection and conversion of action potentials into a digital value (e.g., 0 or 1) directly on the disclosed sensing device to reduce noise and power consumption.

Some aspects of the present disclosure are directed to methods for fabricating intraspinal passive and active (CMOS based) neural probes configured to sense or stimulate the white matter of the spinal cord. In some aspects of the present disclosure, the probes are implemented using either protruding flat or nanopillar electrode arrays or micropillar electrode arrays. In one aspect of the present disclosure, the nanopillar or micropillar arrays are employed to increase an electrode charge density to deliver more efficient stimulating pulses. For example, implementations of the nanopillars or micropillars employ either lower stimulating voltage or shorter pulses, resulting in less heat transfer to the surrounding tissue which means less tissue damage to patients.

In some aspects of the present disclosure, the nanopillars and/or micropillars are arranged periodically with constant spacing or arranged aperiodically, in a fractal-like pattern, in order to increase the electrode adaptability to the target tissue. For example, muscle innervation exhibits a gradient of nerve ending density, therefore mimicking such gradient when stimulating that muscle may be beneficial. In some aspects of the present disclosure, the nanopillar or micropillar stiffness can be tailored according to the target tissue where implantation will occur in order to decrease tissue inflammation, increase tissue adhesiveness, and therefore lengthening the duration of continuous electrical cellular recording and or stimulation.

For example, the nanopillar and/or micropillar stiffness can be modified by changing the diameter (2r) or the height (L). The bending stiffness (K) that the cell will feel is directly related to the second moment of inertia (I) of the post, which depends primarily on the radius of the nanoneedle and is inversely related to the third power of the height of the nanoneedle (L) as indicated by the following equation: $\kappa=3EI/L^3$. For instance, in one configuration that exhibits nanoneedles made of an amorphous silicon core coated in titanium nitride (TiN), a compliant nanopillar (r=25 nm, H=5 μm) exhibits an estimated κ=43 nN/m, while a stiff nanopillar (r=500 nm, H=2.5 μm) exhibits an estimated κ=36 N/m. The composite Young's modulus (E) of the pillar (Si coated with 40 nm TiN) was estimated to be 60 GPa, and the area moment of inertia (I) for a circle (πr+/4) was used.

In a proposed spinal sensing device of a passive type, a nanoneedle array is fabricated. In this example, the nanoneedle array is fabricated on an insulated substrate, such as thermal silicon oxide ($SiO_2$). In this configuration, the nanoneedle array is composed of vertical nanoscale posts built on flat square electrodes of controlled size ranging from $5\times5$ microns$^2$ to $100\times100$ microns$^2$. In other configurations, both the nanoscale posts and the square electrode substrates are coated with a conductive material including, but not limited to, titanium nitride (TiN), gold (Au), and/or platinum (Pt). In a further configuration, a flat portion of the electrode is insulated with an insulator or insulator stack made of such materials as, but not limited to, $SiO_2$, silicon nitride (SiN), hafnium oxide ($HfO_2$), titanium dioxide ($TiO_2$), and aluminum oxide ($Al_2O_3$), while the vertical portion of the posts exhibit an electrically conductive surface composed of materials, such as, but not limited to, TiN, Au, and Pt. Additionally, 3D features of the nanoneedles range from 30-250 nanometers in radius (r), 1-5 microns in height (L). The number of nanoneedles per electrode made by a square opening of $30\times30$ μm$^2$ ranges from 900 to 2500 nanoneedles.

According to an aspect of the present disclosure, a spinal sensing device is described. In one configuration, the spinal sensing device includes means for sensing a neural signal from a spinal cord and/or a medulla of a patient. For example, the sensing means may be the sensing electrodes 310/410 of FIGS. 3 and/or 4. In one configuration, the spinal sensing device includes means for encoding an action potential of a patient into a digital signal. For example, the encoding means may be the ADC stage 350/450 of FIGS. 3 and 4. In another aspect, the aforementioned means may be any module, or any apparatus or material configured to perform the functions recited by the aforementioned means.

Figure 9A:
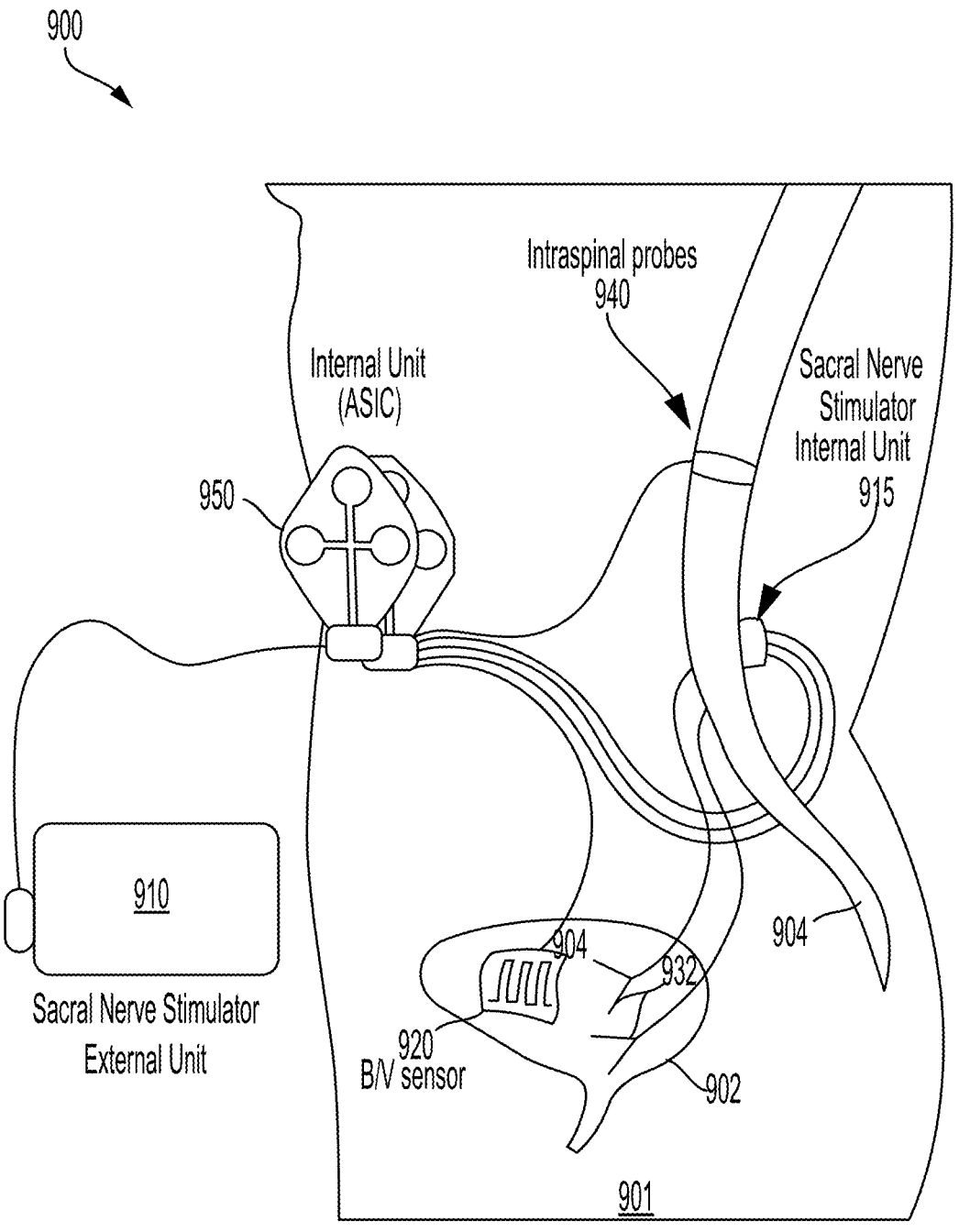
FIGS. 9A and 9B are schematic and block diagrams illustrating of a bi-directional, closed-loop bladder control device system, according to some aspects of the present disclosure.
Figure 9B:

FIGS. 9A and 9B are schematic and block diagrams illustrating of a bi-directional, closed-loop bladder control device system, according to some aspects of the present disclosure. As shown in FIG. 9A, the closed-loop bladder control device system 900 is controlled by an application-specific IC (ASIC) device 950, which coordinates the activities of the closed-loop bladder control device system 900.

As shown in FIG. 9B, the individual components of the ASIC device 950 are assembled in a functional unit controlled by a digital core and configured to interface with a sacral anterior root stimulator (SARS) 930 to re-establish sensory and motor control of bladder functions of a bladder 902 in a paralyzed person 901, as shown in FIG. 9A. In some aspects of the present disclosure, the SARS unit 930 is composed of a sacral anterior root stimulator (SARS) external unit 910 which transfers power to an internal unit 915 (see FIG. 9B) that is placed subcutaneously, as shown in FIG. 9A. In this configuration, the internal unit 912 is connected to stimulating leads 932 that contact the sacral nerve 904 and deliver voltage controlled biphasic pulses to trigger bladder contraction. For example, the external unit 910 is able to send power to the internal unit 915 using various carrier frequencies (e.g., 7 MHz and 9 MHz).

In some aspects of the present disclosure, the ASIC device 950 is configured using CMOS technology to perform the flowing process 1000, as shown FIG. 10. In this configuration, the ASIC device is configured to (1002) harvest the power coming from one or more channels of the SARS external unit 910; (1004) sense a pressure/volume of a bladder 902 using a bladder volume (B/V) sensor 920; (1006) perform intraspinal stimulation using the SARS internal unit 910; (1008) receive information from the intraspinal sensing chip 960; and (1010) transmit a 1-bit sensory signals out to the SARS external unit 910 of the SARS unit 930 for triggering the SARS internal unit 910 to activate the stimulating leads 932 that contact the sacral nerve 904 and deliver voltage controlled biphasic pulses to trigger bladder contraction.

In some aspects of the present disclosure, the bladder control scheme process 1000, involves sending power from the SARS external unit 910 to a power bank which is built into the ASIC device 950. In operation, the bladder volume (BV) sensor 920 uses a fraction of this power to monitor bladder wall tissue impedance at 1 Hz when a BV<$V_{threshold}$ (threshold voltage ($V_{th}$)). Once the bladder volume is greater than the threshold voltage (e.g., BV>$V_{th}$) the B/V sensor 920 collects data for 10 seconds using an integrator (e.g., a bladder sensor readout unit 980), which will turn on intraspinal probes 940 if BV>$V_{th}$ for this period of time. When the intraspinal probes 940 are on, the B/V sensor 920 turns off. In some aspects of the present disclosure, the intraspinal stimulator 970 use a single channel to stimulate the afferent micturition center. In some aspects of the present disclosure, identification of this channel is carried out before a surgical procedure is complete by applying stimulation pulses to each of 32 channels (one at a time), while monitoring which of the channels triggers a urination reflex or bladder contractions in animals while paralyzed human patients would be asked when they feel an urge to urinate.

In operation, the intraspinal stimulator 970 may deliver a biphasic current pulse ranging from 30-180 uA with each phase lasting 100-200 us and having a frequency that can range from 10-125 Hz. In this example, the intraspinal probes 940 continue stimulating until a signal is received by the intraspinal sensing chip 960, which indicates the patient's intention to void. For example, the recorded signals (e.g., 0 or 1) represent the presence or absence of action potentials in the micturition afferent area and are relayed on the transmitting unit 962 which will communicate with the SARS external unit 910 that activate the SARS unit 930, resulting in bladder contractions. The relatively slow sensing probe sampling rate (10 kHz) combined with the small number of recording pixels (32) and 1-bit digitization allows for a light data rate of 320 kb/s for uncompressed data.

For a firmware and/or software implementation, the methodologies may be implemented with modules (e.g., procedures, functions, and so on) that perform the functions described herein. A machine-readable medium tangibly embodying instructions may be used in implementing the methodologies described herein. For example, software codes may be stored in a memory and executed by a processor unit. Memory may be implemented within the processor unit or external to the processor unit. As used herein, the term "memory" refers to types of long term, short term, volatile, nonvolatile, or other memory and is not to be limited to a particular type of memory or number of memories, or type of media upon which memory is stored.

If implemented in firmware and/or software, the functions may be stored as one or more instructions or code on a computer-readable medium. Examples include computer-readable media encoded with a data structure and computer-readable media encoded with a computer program. Computer-readable media includes physical computer storage media. A storage medium may be an available medium that can be accessed by a computer. By way of example, and not limitation, such computer-readable media can include RAM, ROM, EEPROM, CD-ROM or other optical disk storage, magnetic disk storage or other magnetic storage devices, or other medium that can be used to store desired program code in the form of instructions or data structures and that can be accessed by a computer. Disk and disc, as used herein, include compact disc (CD), laser disc, optical disc, digital versatile disc (DVD), and Blu-ray disc, where disks usually reproduce data magnetically, while discs reproduce data optically with lasers. Combinations of the above should also be included within the scope of computer-readable media.

In addition to storage on computer-readable medium, instructions and/or data may be provided as signals on transmission media included in a communication apparatus. For example, a communication apparatus may include a transceiver having signals indicative of instructions and data. The instructions and data are configured to cause one or more processors to implement the functions outlined in the claims.

Although the present disclosure and its advantages have been described in detail, it should be understood that various changes, substitutions and alterations can be made herein without departing from the technology of the disclosure as defined by the appended claims. For example, relational terms, such as "above" and "below" are used with respect to a substrate or electronic device. Of course, if the substrate or electronic device is inverted, above becomes below, and vice versa. Additionally, if oriented sideways, above and below may refer to sides of a substrate or electronic device. Moreover, the scope of the present application is not intended to be limited to the particular configurations of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding configurations described herein may be utilized, according to the present disclosure. Accordingly, the appended claims are intended to include within their scope such processes, machines, manufacture, compositions of matter, means, methods, or steps.

Those of skill would further appreciate that the various illustrative logical blocks, modules, circuits, and algorithm steps described in connection with the disclosure herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the disclosure herein may be implemented or performed with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, multiple microprocessors, one or more microprocessors in conjunction with a DSP core, or any other such configuration.

The steps of a method or algorithm described in connection with the disclosure may be embodied directly in hardware, in a software module executed by a processor, or in a combination of the two. A software module may reside in RAM, flash memory, ROM, EPROM, EEPROM, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary designs, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can include RAM, ROM, EEPROM, CD-ROM or other optical disk storage, magnetic disk storage or other magnetic storage devices, or any other medium that can be used to carry or store specified program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD) and Blu-ray disc where disks usually reproduce data magnetically, while discs reproduce data optically with lasers. Combinations of the above should also be included within the scope of computer-readable media.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein but is to be accorded the full scope consistent with the language of the claims, wherein reference to an element in the singular is not intended to mean "one and only one" unless specifically so stated, but rather "one or more." Unless specifically stated otherwise, the term "some" refers to one or more. A phrase referring to "at least one of" a list of items refers to any combination of those items, including single members. As an example, "at least one of: a, b, or c" is intended to cover: a; b; c; a and b; a and c; b and c; and a, b and c. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "a step for."

What is claimed is:

1. A spinal sensing and stimulating device, comprising:
a complementary metal oxide semiconductor (CMOS) electrode array, supported by a substrate and comprising a plurality of semiconductor electrodes sized and arranged to enable direct stimulation of specific neurons and/or axons of a medullary/spinal cord implant of a patient; and
a data processing unit configured to digitize a neural signal detected from the medullary/spinal cord implant of the patient through the plurality of semiconductor electrodes of the CMOS electrode array.

2. The spinal sensing and stimulating device of claim 1, in which a semiconductor electrode of the CMOS electrode array comprises a plurality of pillars supported by the substrate.

3. The spinal sensing and stimulating device of claim 2, in which the CMOS electrode array and the plurality of pillars are coated with a conductive material, comprising titanium nitride (TiN), gold (Au), and/or platinum (Pt).

4. The spinal sensing and stimulating device of claim 2, in which the plurality of pillars comprise semiconductor nanopillars and/or semiconductor micropillars.

5. The spinal sensing and stimulating device of claim 4, in which the semiconductor nanopillars and/or the semiconductor micropillars are arranged periodically with constant spacing or arranged aperiodically, in a fractal-like pattern to increase an electrode adaptability to a target tissue.

6. The spinal sensing and stimulating device of claim 4, in which the plurality of pillars comprise a flat portion insulated with an insulator and/or an insulator stack.

7. The spinal sensing and stimulating device of claim 6, in which the insulator and/or the insulator stack comprises silicon oxide ($SiO_2$), silicon nitride (SiN), hafnium oxide ($HfO_2$), titanium oxide ($TiO_2$), and aluminum oxide ($Al_2O_3$).

8. The spinal sensing and stimulating device of claim 6, in which the plurality of pillars further comprise a vertical portion coupled to the flat portion and comprising an electrically conductive surface composed of titanium nitride (TiN), gold (Au), and/or platinum (Pt).

9. The spinal sensing and stimulating device of claim 1, in which the CMOS electrode array comprises a nanoneedle array composed of vertical nanoscale posts arranged on a flat electrode.

10. The spinal sensing and stimulating device of claim 1, in which the substrate comprises an insulated silicon substrate, having a thermal silicon oxide ($SiO_2$) layer.

11. The spinal sensing and stimulating device of claim 1, in which the data processing unit is further configured to generate a digital zero (0) in response to an action potential detected from the neural signal, and a digital one (1) in response to an absence of the detection of the action potential from the neural signal.

12. The spinal sensing and stimulating device of claim 1, in which the data processing unit is further configured to determine a mental state of the patient according to the neural signal detected from the patient.

* * * * *